(12) United States Patent
Al-Ramadi et al.

(10) Patent No.: US 9,968,641 B2
(45) Date of Patent: May 15, 2018

(54) METHOD TO SUPPRESS THE SYSTEMIC TOXICITY OF CHEMOTHERAPEUTIC DRUGS

(71) Applicant: United Arab Emirates University, Al-Ain (AE)

(72) Inventors: Basel Al-Ramadi, Abu Dhabi (AE); Hakam El-Taji, Abu Dhabi (AE); Maria J Fernandez-Cabezudo, Abu Dhabi (AE); Fawaz Torab, Abu Dhabi (AE)

(73) Assignee: United Arab Emirates University, Al-Ain (AE)

( * ) Notice: Subject to any disclaimer, the term of this patent is extended or adjusted under 35 U.S.C. 154(b) by 0 days. days.

(21) Appl. No.: 14/042,818

(22) Filed: Oct. 1, 2013

(65) Prior Publication Data
US 2014/0212506 A1   Jul. 31, 2014

Related U.S. Application Data

(60) Provisional application No. 61/757,096, filed on Jan. 26, 2013.

(51) Int. Cl.
*A61K 35/644* (2015.01)
*A61K 31/337* (2006.01)
*A61K 45/06* (2006.01)

(52) U.S. Cl.
CPC .......... *A61K 35/644* (2013.01); *A61K 31/337* (2013.01); *A61K 45/06* (2013.01)

(58) Field of Classification Search
None
See application file for complete search history.

(56) References Cited

U.S. PATENT DOCUMENTS

| 5,731,334 A | * | 3/1998 | Wrasidlo | ............. | C07D 305/14 |
| | | | | | 514/358 |
| 6,365,191 B1 | * | 4/2002 | Burman et al. | ............... | 424/489 |
| 2011/0263528 A1 | * | 10/2011 | Keiji | ...................... | A23B 7/154 |
| | | | | | 514/58 |

OTHER PUBLICATIONS 2009 http://www.issaquahpress.com/2009/05/19/brain-cancer-remains-incurable-fatal/.*
Orsolic, Bee honey and cancer, 2009, J ApiProduct and ApiMedical Science, 1: 93-103.*
Allen et al., *A Survey of the Antibacterial Activity of Some New Zealand Honeys*, 43 J. Pharm. Pharmacol. 817-822 (1991).
Al-Waili, *Natural Honey Lowers Plasma Glucose, C-Reactive Protein, Homocysteine, and Blood Lipids in Healthy, Diabetic, and Hyperlipidemic Subjects: Comparison with Dextrose and Sucrose*, 7(1) Journal of Medicinal Food 100-107 (2004).
Bardy et al., *A systemic review of honey uses and its potential value within oncology care*, 17 Journal of Clinical Nursing 2604-2623 (2008).
Fukada et al., *Jungle Honey Enhances Immune Function and Antitumor Activity*, 2011 Evidenced-Based Complementary and Alternative Medicine 1-7 (2011).
Ghashm et al., *Antiproliferative effect of Tualang one on oral squamous cell carcinoma and osteosarcoma cell lines*, 10(49) BMC Complimentary and Alternative Medicine 1-8 (2010).
Gribel et al., 36 Voprosy Onkologii 704-709 (1990).
Inoue et al., *Identification of phenolic compound in manuka honey as a specific superoxide anion radical scavenger using electron spin resonance (ESR) and liquid chromatography with coulometric array detection*, 85 J. Sc. Food Agric. 872-878 (2005).
Jaganathan et al., *Effect of Honey and Eugenol and Ehrlich Ascites and Solid Carcinoma*, 2010 Journal of Biomedicine and Biotechnology 1-5 (2010).
Jänicke, MCF-7 breast carcinoma cells do not express caspase-3, 117 Breast Cancer Res. Treat. 219-221 (2009).
Jänicke et al., *Capase-3 Is Required for DNA Fragmentation and Morphological Changes Associated with Apoptosis*, 273 J. Biol. Chem. 9357-9360 (1998).
Jenkins et al., *Effect of manuka honey on the expression of universal stress protein A in meticillin-resistant Staphylococcus aureus*, 37 International Journal of Antimicrobial Agents 373-376 (2011).
Kwakman et al., *Two Major Medicinal Honeys Have Different Mechanisms of Bactericidal Activity*, 6 PLOS One e17709 (2011).
Mavric et al., *Identification and quantification of methylglyoxal as the dominant antibacterial constituent of Manuka (Leptospermum scoparium) honeys from New Zealand*, 52 Mol. Nutr. Food Res. 483-489 (2008).
Molan, *Potential of Honey in the Treatment of Wounds and Burns*, 2(1) Am. J. Clin. Dermatol. 13-19 (2001).
Rao et al., *Inhibitory effect of Caffeic Acid Esters on Azoxymethane-induced Biochemical Changes and Aberrant Crypt Foci Formation in Rat Colon*, 53 Cancer Research 4182-4188 (1993).
Swellam et al., *Antineoplastic activity of honey in an experimental bladder cancer implantation model: In vivo and in vitro studies*, 10 International Journal of Urology 213-219 (2003).
Tonks et al., *Honey stimulates inflammatory cytokine production from monocytes*, 21 Cytokine 242-247 (2003).
Tonks et al., *A 5.8-kDa component of manuka honey stimulates immune cells via TLR4*, 82 Journal of Leukocyte Biology 1147-1155 (2007).
Weston et al., *Antibacterial phenolic components of New Zealand manuka honey*, 64 Food Chemistry 295-301 (1999).
Wijesinghe et al., *Honey in the treatment of burns: a systematic review and meta-analysis of it efficacy*, 122 (1295) NZMJ 47-60 (2009).
Yao et al., *Flavonoids, phenolic acids and abscisic acid in Australian and New Zealand Leptospermum honeys*, 81 Food Chemistry 159-168 (2003).

(Continued)

*Primary Examiner* — Terry A McKelvey
*Assistant Examiner* — Catheryne Chen
(74) *Attorney, Agent, or Firm* — Buchanan Ingersoll & Rooney PC

(57) ABSTRACT

This invention relates to use of manuka honey in the treatment of cancer. The invention is also directed to the combination of manuka honey with other chemotherapeutic agents to reduce the toxicity of the treatment.

9 Claims, 12 Drawing Sheets

(56) References Cited

OTHER PUBLICATIONS

Bhatia et al., *Treatment of Metastatic Melanoma: An Overview*, 23(6) Oncology 488-496 (May 2009).
Paclitaxel—Cancer Drug Information, National Cancer Institute http://www.cancer.gov/cancertopics/druginfo/paclitaxel (posted Oct. 5, 2006, updated Sep. 18, 2014).
Priyadarshini et al., *Paclitaxel Against Cancer: A Short Review*, 2(7) Medicinal Chemistry 139-141 (2012).
*What Is Cancer?*, National Cancer Institute http://cancer.gov/cancertopics/cancerlibrary/what-is-cancer p. 1-3 (printed on Oct. 26, 2014).

\* cited by examiner

METHOD TO SUPPRESS THE SYSTEMIC TOXICITY OF CHEMOTHERAPEUTIC DRUGS

CROSS-REFERENCE TO RELATED APPLICATIONS

This application is claims priority to U.S. Provisional Application Ser. No. 61/757,096, filed on Jan. 26, 2013, incorporated herein by reference in its entirety for all purposes.

FIELD OF THE INVENTION

This invention relates to a method to suppress the toxicity associated with chemotherapeutic drugs for patients subjected to such treatment. The invention also relates to methods to administer the chemotherapeutic drug in combination with manuka honey in prescribed combination. The combination treatment of manuka honey plus chemotherapeutic drug maintains effective anti-cancer therapy while simultaneously decreasing nonspecific drug toxicity. The invention also relates to a method to treat cancer comprising administering manuka honey.

BACKGROUND OF THE INVENTION

It is becoming a conventional therapy to treat solid tumors with chemotherapeutic drugs. Most of such drugs are associated with toxicities that affect the well being of patients subjected to such therapy. For example, despite the fact that paclitaxel, also known as Taxol, is one of the most potent and effective chemotherapeutic agents in the treatment of solid tumors, including stage 4 disease, a major drawback of the drug is its toxic effects on the bone marrow. In some cases it may also cause an anaphylactic shock, which may be fatal in spite of prophylactic hydrocortisone, and benadryl IV. Common side effects of paclitaxel include nausea and vomiting, loss of appetite, change in taste, thinned or brittle hair, joint pain in arms or legs, changes in color of nails, tingling in the hands or toes. More serious side effects include unusual bruising or bleeding, pain, redness and swelling at the injection site, changes in normal bowel habit, fever, chills cough, sore throat, difficulty swallowing, dizziness, shortness of breath, severe exhaustion, skin rash, facial flushing, female infertility by ovarian damage, and chest pain. Clinical toxicity of paclitaxel is associated with the solvent Cremophor EL in which it is dissolved for delivery.

Attempts at reducing toxicity of Taxanes, the class of medicines that includes compounds such as paclitaxel and docetaxel, have so far failed. Abraxane is an example; Abraxane (nab-paclitaxel) is paclitaxel bound to albumen nanoparticles. Abraxis BioScience developed Abraxane to reduce toxicity of paclitaxel by replacing the toxic solvent delivery method with Albumen. But clinical trials failed to show any advantage. The toxicity of paclitaxel is such that patients taking the drug are better off sleeping overnight in hospital. Mortality is high from bone marrow depression with low WBC with resulting septicemia and irreversible shock.

Honey has been used for more than 2000 years as traditional medicine in different cultures, particularly for its wound healing properties. The antimicrobial properties of honey have been well described in the literature. Intrinsic properties of honey like high osmolarity and acidity, as well as the presence of flavonoids and phenolic acids are responsible for its antibacterial and antioxidant activities (Watson et al. *Food Chem* 64: 295-301, 1999). In addition to its antimicrobial, antioxidant and tissue-protective activities, recent reports have highlighted multiple roles for honey in enhancing immune responses, including the induction of inflammatory cytokine production by macrophages (Tonks et al. *Cytokine* 21: 242-247, 2003), stimulation of neutrophil migration (Fukuda et al. *Evid Based Complement Alternat Med,* 2009) and enhanced antibody production (Al-Waili, *J Med Food* 7: 100-107, 2004). Whether the multitude of honey activities is mediated by the same or different active fractions remains to be fully elucidated.

Manuka honey, obtained from nectar collected by honey bees (Apis Mellifera) from the New Zealand manuka tree (*Leptospermum scoparium*), is a complex mixture of carbohydrates, fatty acids, proteins, vitamins and minerals containing various kinds of phytochemicals with high phenolic and flavonoid content (Yao et al. *Food Chemistry* 81: 159-168, 2003). While manuka honey shares constituents, e.g. glucose-oxidases, with other honeys it also contains other phytochemical factors that potentiate its antibacterial activity like methylglyoxal (Mavric et al., *Mol Nutr Food Res* 52: 483-489, 2008). This gave rise to a classification system adopted for active manuka honey, known as unique manuka factor (UMF), an indication of its antibacterial activity (Allen et al. *J Pharm Pharmacol* 43: 817-822, 1991).

Previous studies addressing the mechanisms of the antibacterial activity of manuka honey identified a number of potential active constituents, including several phenolic compounds that act as scavengers of superoxide anion radicals (Inoue et al., *J Sci Food Agri* 85: 872-878, 2005, Jenkins et al, Jenkins et al. *Int J Antimicrob Agents* 37: 373-376, 2011, Kawakman et al, *PLoS One* 6: e17709, 2011). There is evidence that the antibacterial activity of manuka honey is independent of its role in inducing inflammatory cytokines during innate immune responses.

A 5.8 kD, heat-sensitive, protease-resistant, component, that was devoid of any antibacterial activity was identified to be responsible for the induction of cytokine production via interaction with TLR4 on macrophages (Tonks et al. *J Leukoc Biol* 82: 1147-1155. 2007). These studies suggest the presence of unique, yet-to-be-characterized, constituents with desired activities in manuka honey. However, an investigation of the anti-proliferative properties of manuka honey has not been undertaken.

Perhaps, one of the oldest known uses for honey is in wound healing. There is extensive scientific and clinical evidence to support the utilization of honey for wounds, skin reactions and damage to epithelial barriers following radiotherapy and chemotherapy (Bardy et al, *J Clin Nurs* 17: 2604-2623 2008). In patients with chronic wounds or burns, honey has been shown to stimulate angiogenesis and epithelialization, promoting more efficient healing (*Molan Am J Clin Dermatol* 2: 13-19 2001, Wijesinghe *N Z Med J* 122: 47-60, 2009). More recently, several reports demonstrated that honey, being rich in polyphenols and flavonoids, has anti-proliferative effects against cancer cells (Jaganathan et al. *J Biomed Biotechnol* 2009: 830616, 2009, Ghashm et al. *BMC Complement Altern Med* 10: 49, 2010, Swellam et al. *Int J Urol* 10: 213-219, 2003). However, the mechanisms for the anti-cancer effect are still to be fully elucidated. In an early study, honey was shown to exhibit modest anti-tumor, but good anti-metastatic, activities against a number of tumor cell lines (Gribel & Pashinskii *Vopr Onkol* 36: 704-709, 1990). Another study extended this observation and showed that dietary intake of caffeic acid esters, a major constituent of Propolis honey beehives, inhibited the incidence and multiplicity of invasive and non-invasive carcinogen-induced colon adenocarcinomas (Rao et al *Cancer Res* 53:4182-4188, 1993). More recently, diluted unfractionated honey was shown to inhibit the proliferation of bladder cancer cell lines in vitro. Moreover, intralesional injection of honey was found to inhibit tumor growth in a bladder cancer implantation mouse model, but the effect of the treatment on animal survival was not reported (Swellam et al. *Int J Urol* 10: 213-219, 2003).

The effect of manuka honey on the growth of cancer cells, using both in vitro as well as in vivo approaches, was investigated. The findings provide mechanistic evidence for the induction of apoptosis in cancer cells by manuka treatment and further highlight a novel role for systemically-administered manuka honey as both an anti-cancer agent and an adjuvant in combination with standard chemotherapeutic agents. Moreover, the data provides direct evidence that manuka honey administration reverses the systemic toxicity associated with the use of a chemotherapeutic agent, such as paclitaxel.

SUMMARY OF THE INVENTION

The present invention relates to methods of treating cancer in a patient comprising administering to the patient a composition comprising manuka honey.

The invention further relates to methods of treating cancer comprising administering to a patient a chemotherapeutic agent and a composition comprising manuka honey.

Another aspect of the invention relates to methods to maintain anti-oxidant levels in a patient during treatment with a chemotherapeutic agent comprising administering a composition comprising manuka honey to the patient.

Other aspects of the invention also relate to methods to reduce the toxicity of a chemotherapeutic agent in a patient comprising administering a composition comprising manuka honey to the patient.

A further aspect relates to a method of reducing the dose of a chemotherapeutic agent administered to a patient during cancer treatment, comprising administering the chemotherapeutic agent with manuka honey.

Preferably the further chemotherapeutic agent is a taxene. More preferably the chemotherapeutic agent is paclitaxel (taxol), or its pharmaceutically acceptable salt.

Preferably the manuka honey composition is in the form of a solution comprising from about 10% w/v to about 60% w/v manuka honey. Preferably the composition comprises between 20-50% w/v manuka honey. The compositions can comprise 20%, 25%, 30%, 35%, 40%, 45%, or 50% w/v manuka honey.

Suitable forms for the manuka honey include pharmaceutical forms for parenteral administration, in particular forms for administering the manuka honey intravenously.

The manuka honey composition can be administered to the patient sequentially or simultaneously with the chemotherapeutic agent. When administered simultaneously the chemotherapeutic agent and the manuka honey can be in the same or separate compositions.

The manuka honey composition and the chemotherapeutic agent are preferably administered intravenously.

In some embodiments the manuka honey and the chemotherapeutic agent can be administered sequentially. The manuka honey and the chemotherapeutic agent can be administered at least 12 hours apart, at least 1 day apart, at least 2 days apart or at least 3 days apart. In other further embodiments the manuka honey and the chemotherapeutic agent are administered together.

The methods of the present application are useful for the treatment of various diseases, including, for example, breast cancer, lung cancer (such as small cell lung cancer and non-small cell lung cancer), renal cancer, bladder cancer, pancreatic cancer, ovarian cancer, prostate cancer, brain cancer, colorectal cancer, leukemia, lymphoma, multiple myeloma and solid tumors. The methods are particularly suitable for treating skin, colon, ovarian, colon, lung and/or breast cancers. In one embodiment the methods are suitable for treating small cell lung cancer. In further embodiments the methods are suitable for treating colon cancer. In a further embodiment the methods are suitable for treating breast cancer. In a further embodiment the methods are particularly suitable for treating lung cancer. In a further embodiment the methods are particularly suitable for skin cancer. In a further embodiment the methods are suitable for treating ovarian cancer.

The invention further relates to manuka honey for use in treating cancer. In particular, the manuka honey is useful in treating, breast cancer, lung cancer (such as small cell lung cancer and non-small cell lung cancer), renal cancer, bladder cancer, pancreatic cancer, ovarian cancer, prostate cancer, brain cancer, colorectal cancer, leukemia, lymphoma, multiple myeloma and solid tumors. The manuka honey is particularly useful for treating skin cancer, colon cancer, ovarian cancer, colon cancer, lung cancer and/or breast cancer.

The invention further relates to manuka honey for use in combination with a chemotherapeutic agent for treating cancer.

A further aspect of the invention relates to manuka honey for use in combination with a chemotherapeutic agent to maintain anti-oxidant levels in a patient treated with the chemotherapeutic agent.

Another aspect of the invention relates to manuka honey for use in combination with a chemotherapeutic agent to reduce the toxicity of the chemotherapeutic agent in a patient.

A further aspect of the invention relates to manuka honey for use in reducing the dosage of a chemotherapeutic agent administered to a patient. The use comprises administering the manuka honey in combination with the chemotherapeutic agent.

In one embodiment the manuka honey is used as an adjunct therapy to chemotherapy. Preferably the manuka honey is for use as an adjunct therapy to paclitaxel therapy.

The invention further relates to a pharmaceutical composition comprising a chemotherapeutic agent and manuka honey. The composition can be a combined preparation for simultaneous or separate use of the manuka honey and chemotherapeutic agent.

Preferably the pharmaceutical composition is in the form of a solution. Preferably the chemotherapeutic agent and manuka honey are in a form suitable for intravenous administration.

Preferably the pharmaceutical composition comprises 10% to 60% w/v manuka honey. In one embodiment the composition comprises from 20 to 50% w/v manuka honey.

The pharmaceutical composition preferably comprises paclitaxel, or its pharmaceutically acceptable salt, as the chemotherapeutic agent.

The invention also relates to the use of the manuka honey to treat cancer. One embodiment comprises the use of manuka honey when administered with a chemotherapeutic agent to treat cancer.

The invention also relates to the use of manuka honey and a chemotherapeutic agent in the treatment of cancer.

The invention further relates to the use of manuka honey to reduce the dose of paclitaxel given to a patient.

Preferably the invention relates to the use of manuka honey in combination with paclitaxel.

The term treatment is intended to include curing, reversing, alleviating, palliative and prophylactic treatment of the condition.

The term "combination therapy" means the administration of two or more therapeutic agents to treat a therapeutic condition or disorder described in the present disclosure. Combination therapy encompasses co-administration of these therapeutic agents, in a substantially simultaneous manner, either in the same composition or in separate compositions independently administered.

In one embodiment the manuka honey and chemotherapeutic agent are formulated into the same composition at an appropriate final concentration for administration to the patient together in one injection.

In some embodiments the administration of the chemotherapeutic agent and the manuka honey composition is concurrent, i.e. the administration period of the chemotherapeutic agent and the administration period of the manuka honey composition overlap. In some embodiments concurrent administration includes starting the administration of the chemotherapeutic agent and the manuka honey composition at the same time. In some embodiments concurrent administration involves starting the administration of one composition after the administration of the first composition has started.

In addition combination therapy encompasses co-administration of each type of therapeutic agent in a sequential manner. Sequential administration of the chemotherapeutic agent and the manuka honey composition can involve administration of the manuka honey composition prior to or after the administration of the chemotherapeutic agent. In some embodiments the administration of the chemotherapeutic agent and the manuka honey composition are non-concurrent. For example the administration of one of the composition is finished before the administration of the other agent begins.

In some embodiments there may be a therapeutically effective time interval between the administration of the paclitaxel and the administration of the manuka honey composition. In some embodiments the time interval between the start of the administration of one of the composition and the start of the administration of the other composition may be about 0.5, 1, 2, 3, 4 or more days. In some embodiments the administration of the first composition is finished before administration of the second composition begins. In certain embodiments the administration of the first agent continues when the administration of the second composition begins.

Patients suffering from cancer are commonly co-administered additional therapeutic agents, in particular anti-neoplastic and/or further anti-tumor agents. Therefore the invention further relates to a combination therapy of paclitaxel and manuka honey in combination with further suitable anti-tumor agents for the treatment of cancer. Suitable agents for co-administering with paclitaxel and manuka honey include for example cisplatin, doxorubicin, trastuzumab. Other suitable agents are also encompassed.

Other therapeutic agents are also commonly administered to patients to deal with the side effects of chemotherapy. Such agents might include anti-emetics for nausea, or agents to treat anaemia & fatigue. Other such medicaments are well known to physicians and others skilled in cancer therapy.

The manuka honey may be formulated for parenteral administration by injection. The compositions may take forms such as suspensions or solutions. The formulations may be presented in unit-dose or multi-dose containers. The compositions may include additional ingredients that are conventional in the art with regard to injectable formulations. Methods of preparing various pharmaceutical compositions are well known to those skilled in the art. Reference is made to 'Remington's Pharmaceutical Sciences'.

In one embodiment the manuka honey can be formulated at the appropriate concentration in a sterile saline solution.

The actual amount of the compositions to be administered, the rate of administration and the time period of administration will depend on a number of factors. These include, for example, the type of cancer to be treated, the chemotherapeutic agent to be used, and the size, location, progression and/or severity of the cancer to be treated. Appropriate dosage and regimes for chemotherapeutic agents such as paclitaxel, are well known in the art.

In some embodiments paclitaxel is administered at a dose of about 75 to 250 mg/m$^2$ over a period of time. The usual dosage of paclitaxel is 135-225 mg/m$^2$ given intravenously for over 3 hours every 2-3 weeks. In a further embodiment paclitaxel is administered at a reduced dosage.

By a reduced dosage of a chemotherapeutic agent it is meant providing the chemotherapeutic in a dosage less than the usual dosage of the chemotherapeutic agent when administered without manuka honey. For example, providing paclitaxel to the patient in a dose smaller than the usual dosage that would otherwise be administered to the patient in the absence of manuka honey during therapy.

The concentration of the manuka honey is typically in the range from 10% w/v to 60% w/v in an aqueous solution. In further embodiments the concentration is in the range from about 10% w/v to about 50% w/v, about 20% to about 50% w/v, and more preferably from about 30% w/v to about 50% w/v. In some embodiments the methods for treating cancer involve infusing the manuka honey composition once every three days. In some embodiments 75-200 ml of a manuka honey composition is infused twice per week, once weekly, once biweekly, or once tri-weekly. Preferably 100 ml of the manuka honey composition is infused with each treatment round provided to the patient.

In some embodiments the method for treating cancer involves intravenously administering about 75 to about 250 mg/m$^2$ of paclitaxel and administering a composition comprising manuka honey at a concentration of 10% to 60% w/v.

Disclosed are combination treatments of paclitaxel with manuka honey that result in a significant improvement in overall animal survival.

The use of manuka honey in combination with paclitaxel has been demonstrated by various in vitro and in vivo models. Although tumor-bearing mice treated with paclitaxel alone exhibited a 60% reduction in tumor growth, their overall survival was only 20%. Tumor-bearing animals treated with manuka honey plus paclitaxel exhibited a similar degree of inhibition in their tumor growth but, in sharp contrast, there was a 3-fold enhancement in animal survival.

Animal toxicity studies, utilizing multiple intravenous administrations of manuka honey, confirmed that systemic administration of manuka honey is not associated with any systemic toxicity. Analysis of hematological (total WBC, neutrophils, lymphocytes, monocytes, RNC and platelets) as well as clinical chemistry (ALT, AST, LDH, creatinine, BUN, and glucose) parameters in manuka honey-injected animals showed no alterations from normal controls. Administration of paclitaxel to animals resulted in a significant decrease in the level of antioxidant in various organs. However, simultaneous treatment with paclitaxel plus unique concentrations of manuka honey was found to reverse the taxol-induced deleterious effects on organ antioxidant levels.

The combination of manuka with paclitaxel is effective in reducing overall toxicity, leading to improved animal survival and effective control of tumor proliferation. This combination of effects, namely effective control of cancer growth and reduced tissue toxicity, may potentially represent a breakthrough in cancer treatment.

Manuka honey has been recognized for its anti-bacterial and wound-healing activity but its potential antitumor effect is poorly studied despite the fact that it contains many antioxidant compounds. Disclosed is a combination that demonstrates anti-proliferative activity of manuka honey on three different cancer cell lines in vitro, murine melanoma (B16.F1) colorectal carcinoma (CT26) and human breast cancer (MCF-7) cells. The invention demonstrates that manuka honey has potent anti-proliferative effect on all three cancer cell lines in a time and dose-dependent manner, being effective at concentrations as low as 0.6% (w/v). Without being bound by any hypothesis, it is believed that this effect is mediated via the activation of a caspase 9-dependent apoptotic pathway, leading to the induction of caspase-3, reduced Bcl-2 expression, DNA fragmentation and cell death. Combination treatment of cancer cells with manuka plus paclitaxel in vitro, however, revealed no evidence of a synergistic action on cancer cell proliferation. Furthermore, an in vivo syngeneic mouse melanoma model was utilised to assess the potential effect of intravenously administered manuka honey, alone or in combination with paclitaxel, on the growth of established tumors. The combination indicates that systemic administration of manuka honey was not associated with any alterations in haematological or clinical chemistry values in serum of treated mice, demonstrating its safety profile. Treatment with manuka honey alone resulted in about 33% inhibition of tumor growth, which correlated with histologically observable increase in tumor apoptosis. Although better control of tumor growth was observed in animals treated with paclitaxel alone or in combination with manuka honey (61% inhibition), a dramatic improvement in host survival was seen in the co-treatment group. This highlights a role for manuka honey in alleviating chemotherapy-induced toxicity. In summary, the findings demonstrate that:

(1) Manuka honey is able to inhibit the growth of different cancer cell lines (e.g. human breast cancer, murine colon cancer and murine melanoma) in vitro, even at exceedingly low concentrations (<1%).

(2) Manuka exerts its anti-cancer activity via the activation of caspase 9-dependent, intrinsic, apoptosis pathway. This is in sharp contrast to paclitaxel that induces cancer cell death via the activation of a caspase 8-dependent, extrinsic apoptosis pathway.

(3) When used in an experimental animal melanoma model, the combination of manuka plus paclitaxel resulted in effective inhibition of tumor growth and a marked enhancement in animal survival.

(4) When used in combination with paclitaxel, manuka reverses systemic, chemotherapy associated, organ toxicities.

BRIEF DESCRIPTION OF THE FIGURES

The accompanying drawings, which are incorporated in and form a part of the specification, illustrate embodiments of the presently disclosed invention and, together with the description, disclose the principles of the invention.

DESCRIPTION OF THE INVENTION

Despite the remarkable advances made over the past 50 years in understanding the basis of cancer development, and the increased availability of treatment modalities, cancer-related death toll remains one of the highest among chronic human diseases. A major concern for anti-cancer drugs is their potential toxicity. Considerable efforts continue to be exerted to identify naturally occurring compounds, or their principle active components, with potential to complement existing cancer therapeutic modalities. The current invention highlights several findings regarding the utility of manuka honey as a potential anti-cancer agent. First, multiple intravenous injections of manuka honey, administered over a period of 2-3 weeks, caused no apparent systemic side effects, as judged by the results of the hematological and clinical chemistry analyses which showed no alterations in the cellular constituents of blood or chemical markers of organ dysfunction in the serum of treated animals. Second, manuka honey treatment resulted in a significant growth inhibition (~33%) in a melanoma tumor model known for its aggressiveness and low immunogenicity. Third, several lines of in vitro evidence demonstrate that manuka honey induces death of cancer cells via the activation of caspase-9-dependent intrinsic apoptosis pathway. Finally, intravenous co-administration of paclitaxel and manuka honey resulted in a highly significant inhibition of tumor growth and improved overall animal survival.

In order to demonstrate the invention, experiments were done to study the physiochemical characteristics of the manuka honey. Different dilutions of manuka honey were prepared directly in tissue culture medium in which the B16.F1 melanoma cells are routinely cultured and tested for their pH and osmolarity. The studies revealed that manuka honey solutions of concentrations up to 5% (w/v) were physiological (data not shown). Thus, all subsequent in vitro studies were carried out using manuka honey concentrations in the range of 0.3% to 5%.

For all experiments paclitaxel (Sigma, St Louis, Mo., USA) was initially diluted in sterile saline solution. The drug was further diluted to the desired final concentration in either further sterile saline for i.v. studies or freshly diluted in culture medium for in vitro studies. Manuka honey (UMF 10+, Honeyland NZ Ltd, New Zealand) was diluted in sterile saline or culture medium for in vivo or in vitro studies respectively.

Manuka Honey Inhibits Growth of Cancer Cells

Figure 1:
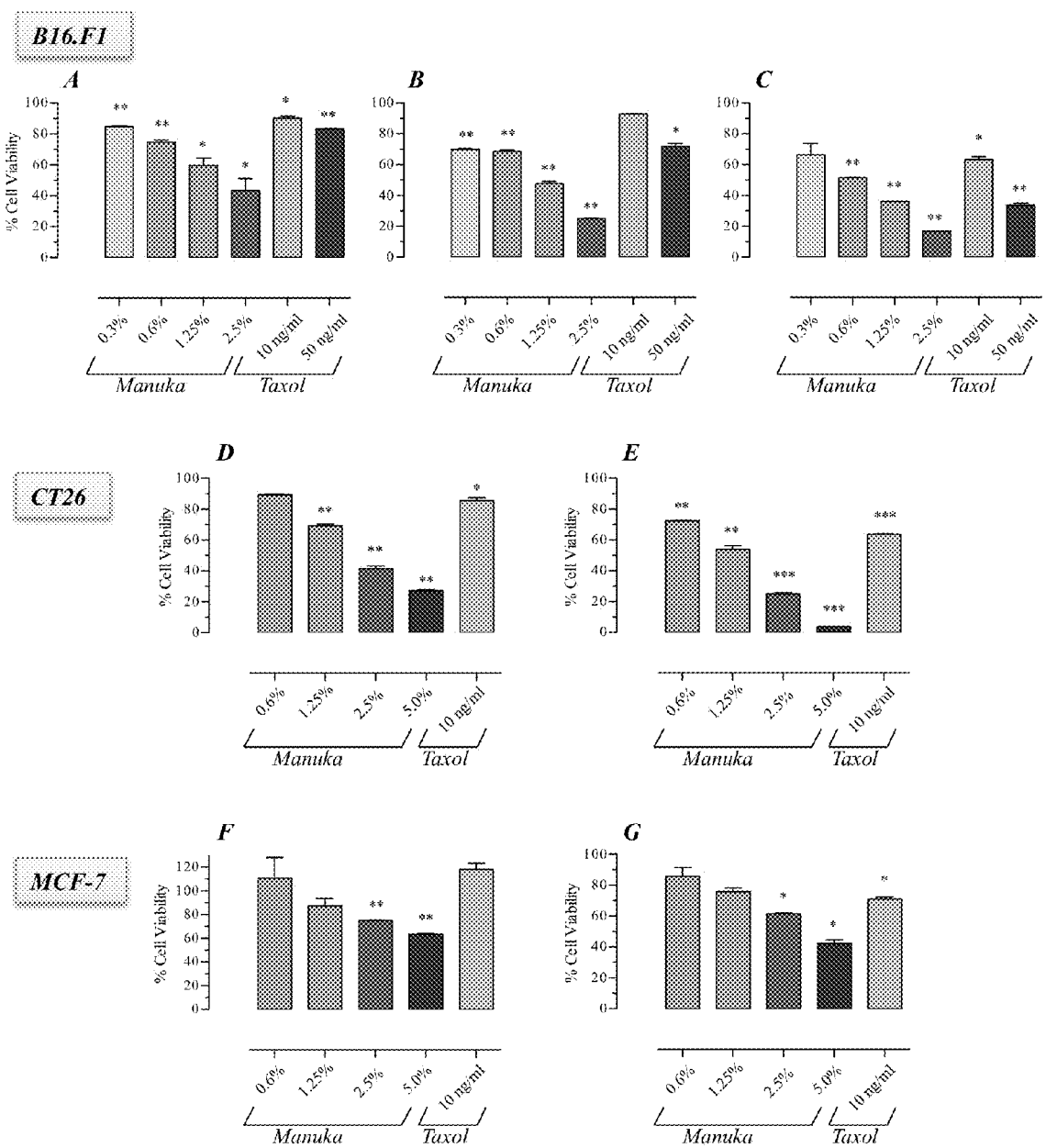
FIG. 1 demonstrates the ability of manuka honey to inhibit cancer cells. Skin cancer cells (B16.F1 cell line) (graphs A-C), colon cancer cells (CT26 cell line) (graphs D, E) and breast cancer cells (MCF-7 cell line) (graphs F, G) were plated at $5 \times 10^3$ cells per well and incubated for 24 hr (graphs A, D, F), 48 hr (graph B) or 72 hr (graphs C, E, G) in the absence or presence of the indicated concentrations of manuka honey (range 0.3% to 5.0% w/v), or taxol (10 ng/ml or 50 ng/ml final concentration). At the end of the incubation period, cell viability was determined using CellTiter-Glo luminescent assay. Results are expressed as percentage viability in treated cell cultures compared to control, untreated, cells and are representative of 3 (for B16.F1 cells) or 2 (for CT26 and MCF-7 cells) independent experiments. Asterisks denote statistically significant differences in viability of experimental groups compared to control (*, $p<0.05$; , $p<0.01$; *, $p<0.001$).

The potential effect of manuka honey on cancer cell proliferation was investigated using three tumor cell lines differing in type and origin, the murine melanoma (B16.F1) and colon carcinoma (CT26) cells and the human breast cancer (MCF-7) cell line. Cells were incubated with different concentrations of manuka honey (range 0.3 to 2.5% w/v) for 24-72 hrs. As a positive control, cells were cultured with taxol at a final concentration of 10 or 50 ng/ml. As shown in FIG. 1, the addition of as little as 0.3% manuka honey to cells in culture resulted in a significant decrease in the viability of B16.F1 cells (panels A-C). This inhibitory effect on cell viability was dependent on both manuka honey concentration and total incubation time. By as early as 24 hrs, the viabilities of B16.F1 cells cultured with manuka honey at final concentrations of 0.3, 0.6, 1.25 and 2.5% were 85%, 75%, 60% and 43% of control (no manuka honey) cultures, respectively (FIG. 1A).

In contrast, over the same time period, the viabilities of B16.F1 cells cultured in presence of 10 ng/ml or 50 ng/ml of the antineoplastic drug taxol were reduced to 90% or 83% of control, respectively (FIG. 1A). The decreased cell viability was more pronounced as the time of culture increased to 48 hrs (FIG. 1B) or 72 hrs (FIG. 1C). At the latter time point, cell viability was reduced to 17% in cell cultures treated with 2.5% manuka honey (FIG. 1C). Under the same conditions, cells cultured with 10 ng/ml or 50 ng/ml taxol had a reduction in viability to 64% or 34% of control, respectively. Essentially similar results were also observed with the CT26 (panels D-E) and MCF-7 (panels F-G) cancer cell lines. These results demonstrate that in vitro treatment of cancer cells with low concentrations of manuka honey resulted in significant inhibition of cell proliferation.

Manuka Honey Induces Apoptosis in Cancer Cells

Figure 2:
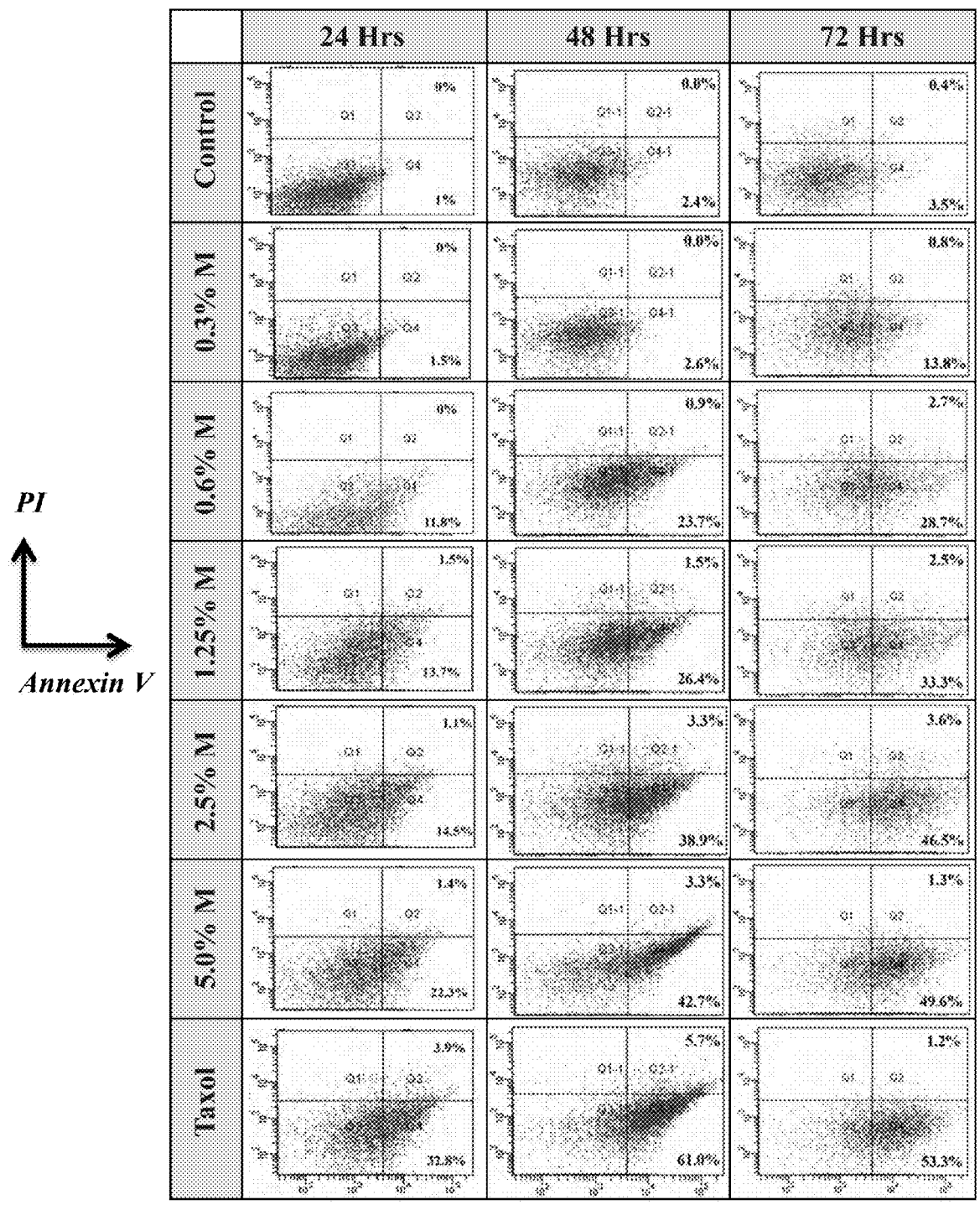
FIG. 2 shows that Manuka honey induces the death of cancer cells by an apoptotic mechanism. B16.F1 cells were treated for 24 hr (left column), 48 hr (center column) or 72 hr (right column) with varying concentrations of manuka honey (M; range 0.3%-5.0%), taxol (10 ng/ml) or medium as control. At the end of the incubation period, cells were harvested and stained with Annexin V and PI, and analyzed by flowcytometry. The percentages of cells in early (Annexin V+, PI−; lower right quadrant) and late apoptotic-necrotic stages (Annexin V+, PI+; upper right quadrant) are shown. The results are representative of three independent experiments.

The potential mechanism by which manuka honey was causing decreased cell viability was addressed. Loss of cell membrane asymmetry, detectable by Annexin V staining, represents one of the earliest events in apoptosis. B16.F1 cells were harvested at 24, 48, or 72 hours after treatment with different concentrations of manuka honey (range 0.3% to 5.0% w/v) or taxol (at a final concentration of 10 ng/ml), stained with Annexin V-FITC and PI, and subjected to flow cytometric analysis. As can be seen in FIG. 2, there was a dose-dependent, and time dependent, increase in the number of cells undergoing apoptosis (Annexin V-positive) after culture with increasing concentrations of manuka honey. At 24 hr post treatment, while the percent of Annexin V-positive cells in untreated control cultures was 1.0%, there were 1.5%, 11.8%, 13.7%, 14.5% and 22.3% apoptotic cells after culture with 0.3%, 0.6%, 1.25%, 2.5% and 5.0% manuka honey solution, respectively (left panels). In contrast, cells treated with taxol alone showed 32.8% apoptotic cells.

Furthermore, in some cultures, a minor population of cells was observed to be positive for both Annexin V-FITC and PI, representing late apoptotic cells. These cells amounted to 1.0-1.5% of total in cell cultures treated with manuka honey (at 0.6% concentration or higher) and 3.9% in cells treated with taxol. The results of cell analysis following similar treatments for 48 and 72 hrs (center and right panels, respectively) demonstrate a similar dose-dependent trend in apoptosis, with the overall levels of apoptotic cells being higher than those observed at 24 hrs. For example, the percentage of total apoptotic cells following treatment with 0.3% manuka honey was 1.5%, 2.6% and 13.8% after 24, 48, and 72 hrs, respectively. The corresponding ratios of cell death following treatment with 1.25% manuka honey suspension were 15.2%, 27.9% and 35.8%, respectively. These findings suggest that the death of cancer cells following exposure to low concentrations of manuka honey occurs via an apoptotic mechanism.

Figure 3:
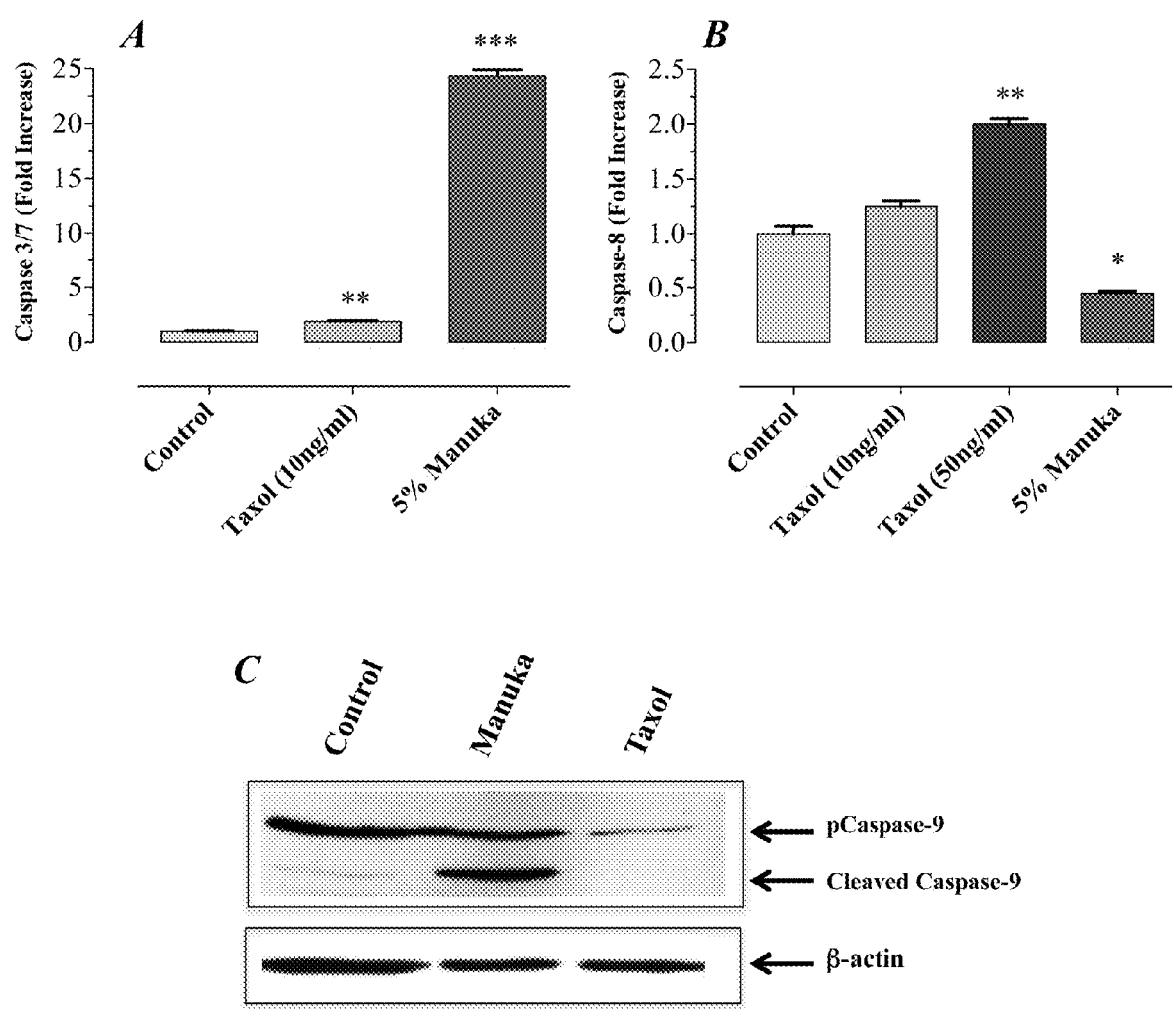
FIG. 3 demonstrates that manuka honey induces the death of cancer cells by activating the intrinsic pathway of caspase-mediated apoptosis. B16.F1 melanoma cells were treated with manuka honey (5% w/v), taxol (10 or 50 ng/ml) or medium as control. After 24 hr of culture, enzymatic activity of caspase 3/7 (graph A) and caspase 8 (graph B) were determined using specific kits and following manufacturer's recommendation. The data is presented as fold increase in caspase activity after normalization to the number of viable cells per culture. C. Western blot analysis of caspase-9 activation B16.F1 cells treated with manuka honey or taxol. Whole cell extracts were prepared after a 24-hr treatment with manuka honey (5% w/v) or taxol (10 ng/ml). Protein extracts were resolved on 10% SDS-PAGE and immunoblotted with caspase-9-specific ployclonal antibody capable of detecting both full length and cleaved forms of caspase-9. The cell extracts were also probed with an antibody against β-actin as a control for protein loading.

A critical component for the initiation of the apoptosis pathway is the sequential recruitment of a number of caspases leading to the activation of the effector caspase-3. This, in turn, leads to the cleavage of a number of vital cellular substrates required for cell viability. Next explored was the mechanism of apoptosis induction in manuka honey-treated cancer cells. B16.F1 melanoma cells exposed to manuka honey (5% w/v final concentration) for 24 hrs exhibited a 24-fold increase in caspase 3/7 activity (FIG. 3A). The induction of caspase 3/7 activity in manuka honey treated cells was mainly due to activation of caspase-9 (FIG. 3C) but not caspase-8 (FIG. 3B).

In sharp contrast, treatment of the cells with paclitaxel (10 ng/ml) led to a 2-fold increase in caspase 3/7 activity (FIG. 3A) and this was associated with a 2-fold increase in caspase-8 activity (FIG. 3B). No evidence for induction of caspase-9 was observed in paclitaxel-treated cancer cells (FIG. 3C). This implies that paclitaxel-induced cell death occurs mainly via the extrinsic pathway, which is in agreement with previous observations. These findings demonstrate that manuka honey activates caspase-dependent apoptosis in cancer cells, a process initiated through caspase-9, implicating the intrinsic pathway in manuka honey-induced cell death.

Bcl-2 is a member of a large family of cell survival-regulating proteins consisting of both pro and anti-apoptotic regulators. Bcl-2 is a pro-survival protein that acts upstream of the caspase pathway and, when overexpressed, can block cell apoptosis. Conversely, inhibition of Bcl-2 protein expression predisposes to apoptosis. Therefore the level of Bcl-2 expression in B16.F1 cells following treatment with manuka honey or taxol was determined. The results, shown in FIG. 4A, demonstrate decreased levels of Bcl-2 protein in manuka honey-treated cancer cells. In taxol-treated cells, Bcl-2 expression was substantially decreased by 24 hr of culture and was undetectable by 72 hr. By contrast, in manuka honey-treated cancer cells, no decrease in Bcl-2 expression was observed at 24 hr; however, by 72 hr, there was >50% reduction in Bcl-2 levels.

Figure 4:
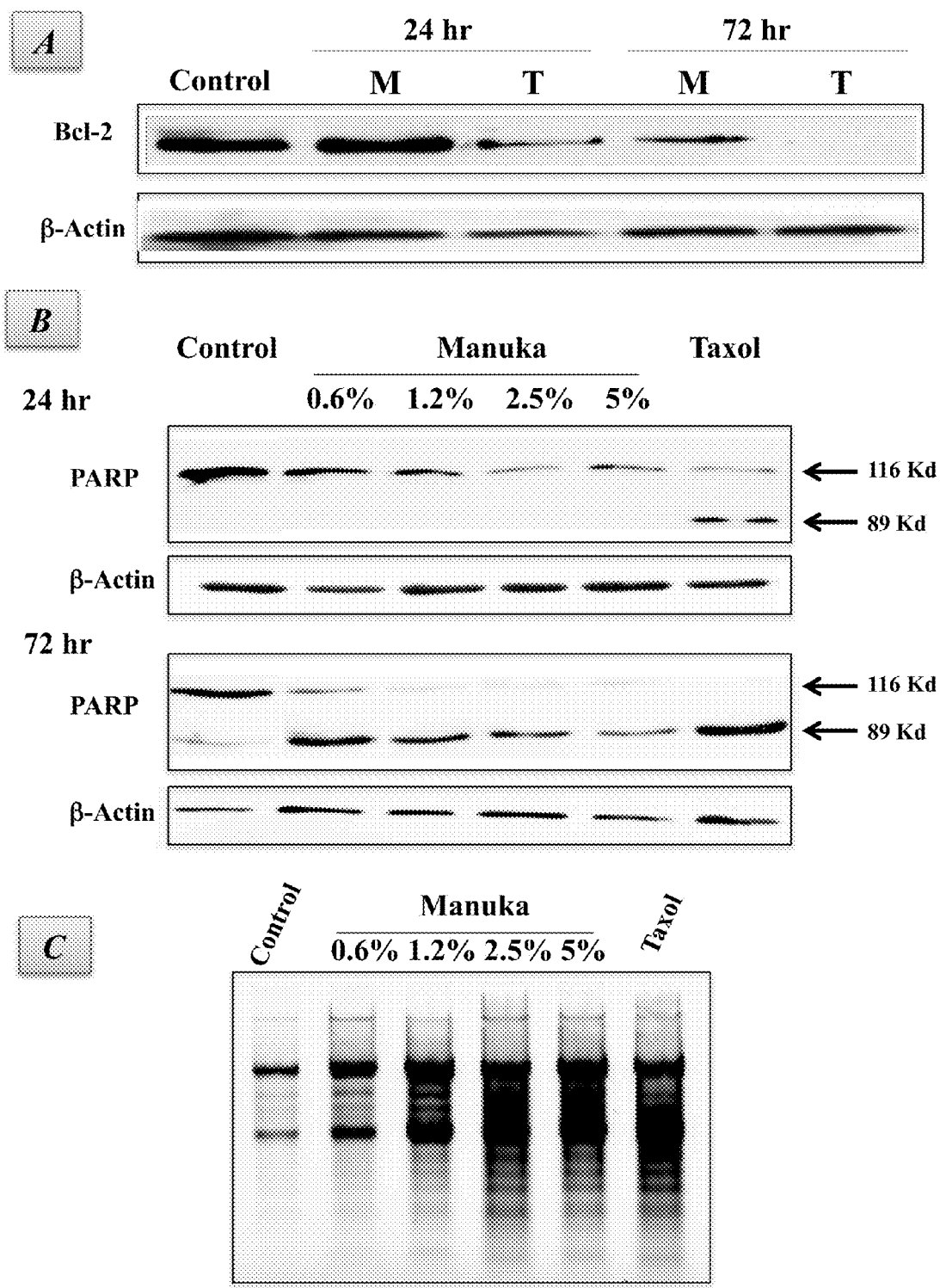
FIG. 4. Manuka honey induces late apoptotic events in cancer cells. A. B16.F1 cells were incubated for 24 hr or 72 hr in the absence or presence of Manuka honey (M; 5%) or taxol (T; 50 ng/ml). Whole cell extracts (100 µg/lane) were resolved on 10% SDS-PAGE followed by Western blotting with an antibody specific to Bcl-2. B. Cells were treated for 24 hr or 72 hr with the indicated concentrations of manuka honey (0.6%-5.0%) or taxol (50 ng/ml). Whole cell extracts (100 µg/lane) were resolved on 10% SDS-PAGE followed by Western blotting with a PARP-specific antibody. The full-length (116 kD) and cleaved (89 kD) forms of PARP are indicated. The cell extracts were also probed with an antibody against β-actin as a control for loading. C. Following treatment for 72 hr, cells were lysed and DNA extracted by centrifugation and phenol-chloroform extraction. Extracted DNA was resolved on 1.5% agarose gel and stained with ethidium bromide to visualize the oligonucleosomal fragments. The results are representative of two independent experiments.

One of the target proteins for active caspase-3 is the DNA repair enzyme poly(ADP-ribose) polymerase (or PARP). So, the effect of manuka honey treatment on caspase-3 activation was investigated by Western blot analysis using a monoclonal antibody against PARP that detects the full length (116 kD) and the cleaved (89 kD) forms of PARP (FIG. 4B). Lysates of B16.F1 cells were prepared following treatment with manuka honey or taxol for 24 hr (upper panels) or 72 hr (lower panels) and subjected to immunoblot analysis with a PARP-specific antibody. After 24 hr of culture, cleavage of PARP into the 89 kD fragment was evident only in taxol-treated cells (upper panel). However, after 72 hr, PARP was cleaved effectively in manuka honey-treated cells in a dose-dependent manner (lower panel). Thus, at concentrations as low as 0.6%, manuka honey can effectively induce the caspase pathway leading to apoptosis of cancer cells.

The effect of manuka honey-induced caspase activation on DNA fragmentation was also analyzed by agarose gel electrophoresis of cellular DNA isolated after treatment. As shown in FIG. 4C, a characteristic ladder pattern representing fragmented DNA was observed in cancer cells following treatment with manuka honey. At the highest manuka honey concentration used (5.0%), the extent of DNA fragmentation, a classical apoptotic feature, was largely equivalent to that observed in taxol-treated cells. Taken together, the above results suggest that manuka honey leads to inhibition of cellular proliferation through a reduction in pro-survival protein expression and activation of apoptosis pathway.

In Vivo Toxicity Studies

Figure 5:
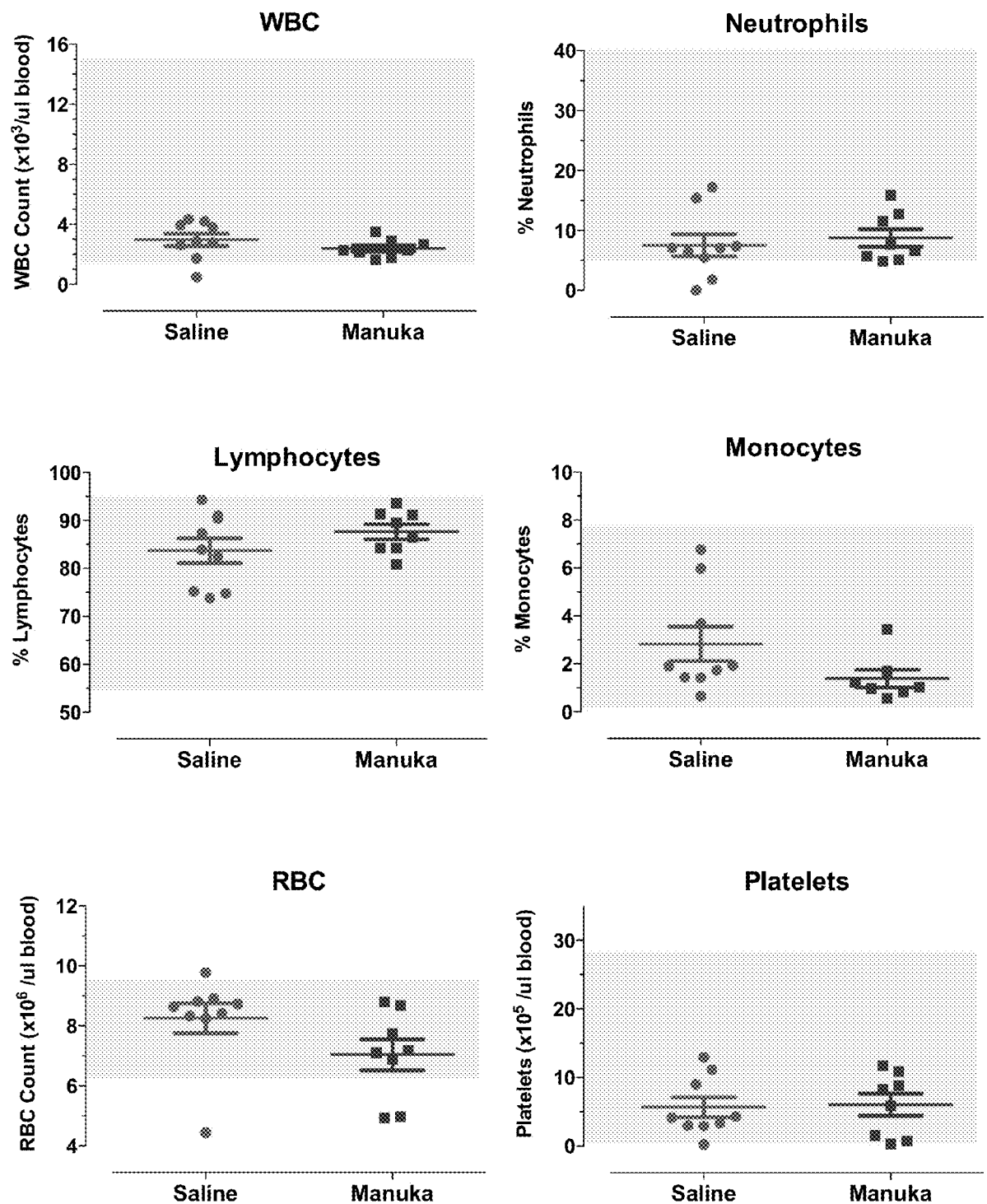
FIGS. 5 and 6 illustrate that systemic administration of manuka honey is not associated with any alterations in hematological values (FIG. 5) or clinical chemistry parameters (FIG. 6). Mice were injected with saline or manuka honey (50% w/v) 2 times per week for a total of 3 weeks, following which blood was collected and analyzed for the indicated parameters. In each graph, the values for individual mice in a group are shown, together with the mean±SEM. The shaded box in each graph represents the normal range for that particular parameter. The results are representative of three independent experiments.
Figure 6:
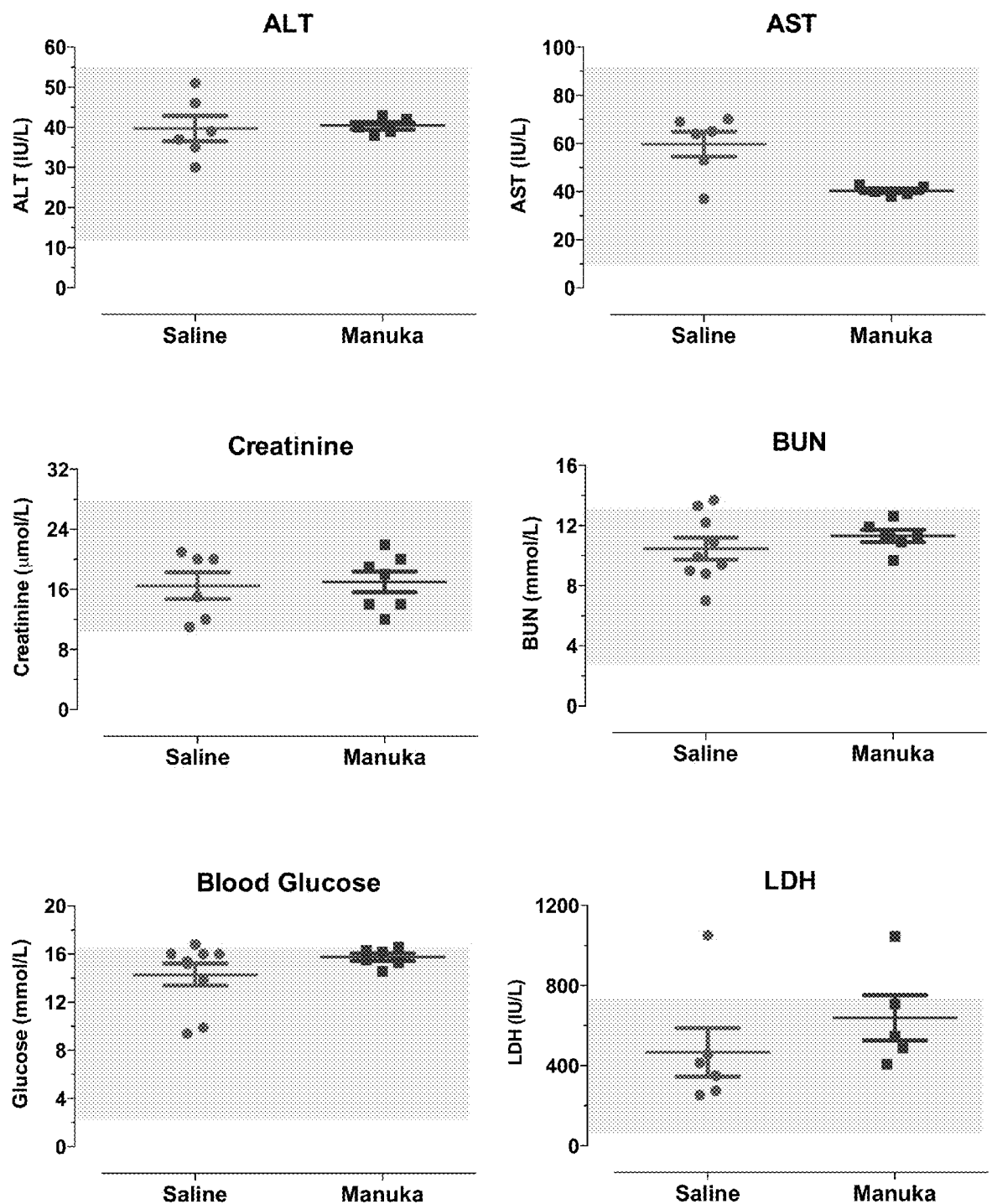

Given the demonstrated in vitro effect of manuka honey on melanoma cells, the potential of using manuka honey in an in vivo animal tumor model was investigated. In preparation for that, a series of experiments was carried out to test for any potential in vivo toxicity associated with intravenous administration of manuka honey. Mice received multiple i.v. injections of 50% (w/v) manuka honey solution diluted in sterile saline for 3 weeks. At the end of this period, animals were sacrificed and blood was collected for hematological and clinical chemistry analysis, the results of which are shown in FIGS. 5 and 6, respectively. The findings demonstrated that multiple i.v. injections of manuka honey were not associated with any alterations in cellular constituents of blood, including total WBC count, RBC count, platelet count, % neutrophils, % lymphocytes and % monocytes (FIG. 5). Furthermore, no significant changes were observed in the levels of various chemical markers of organ dysfunction, including creatinine, BUN, AST, ALT, LDH, and glucose (FIG. 6).

Figure 7:
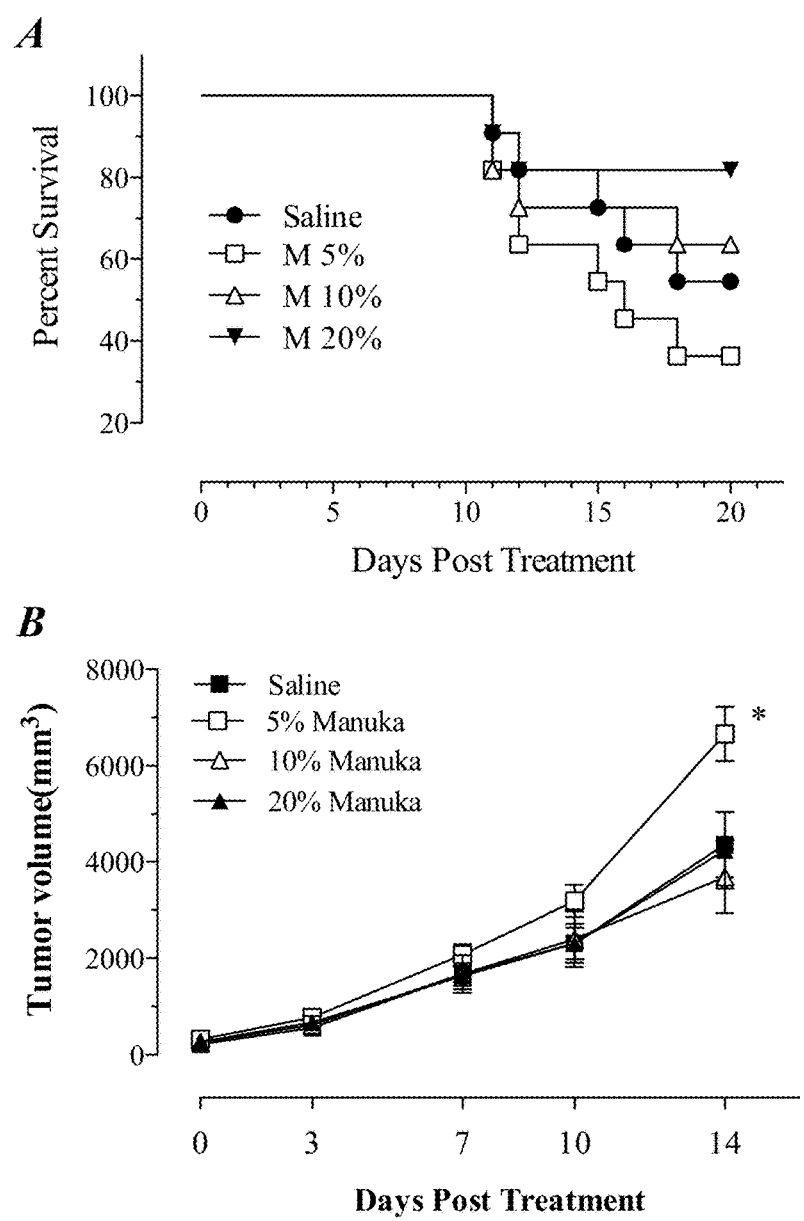
FIGS. 7 A-B show the results from the systemic administration of manuka honey at different concentrations on tumor growth and animal survival. Manuka honey at either 5%, 10%, or 20% w/v, or saline were administered to the animals twice per week until the end of the observation period.

Systemic Administration of Manuka Honey Inhibits Tumor Growth and Enhances Host Survival The activity of manuka honey was evaluated in B16.F1 melanoma tumor model. Mice were divided in four groups and treated by intravenous administration (100-200 μl 2 times per week for up to 3 weeks) of manuka honey alone, at either 5%, 10% or 20% w/v, or saline as a control. Tumor volume and animal survival were followed for up to 3 weeks post treatment initiation. As shown in FIG. 7 the use of manuka honey alone at higher concentrations (10% and 20%) was effective in retarding tumor growth and enhancing animal survival.

Figure 8:
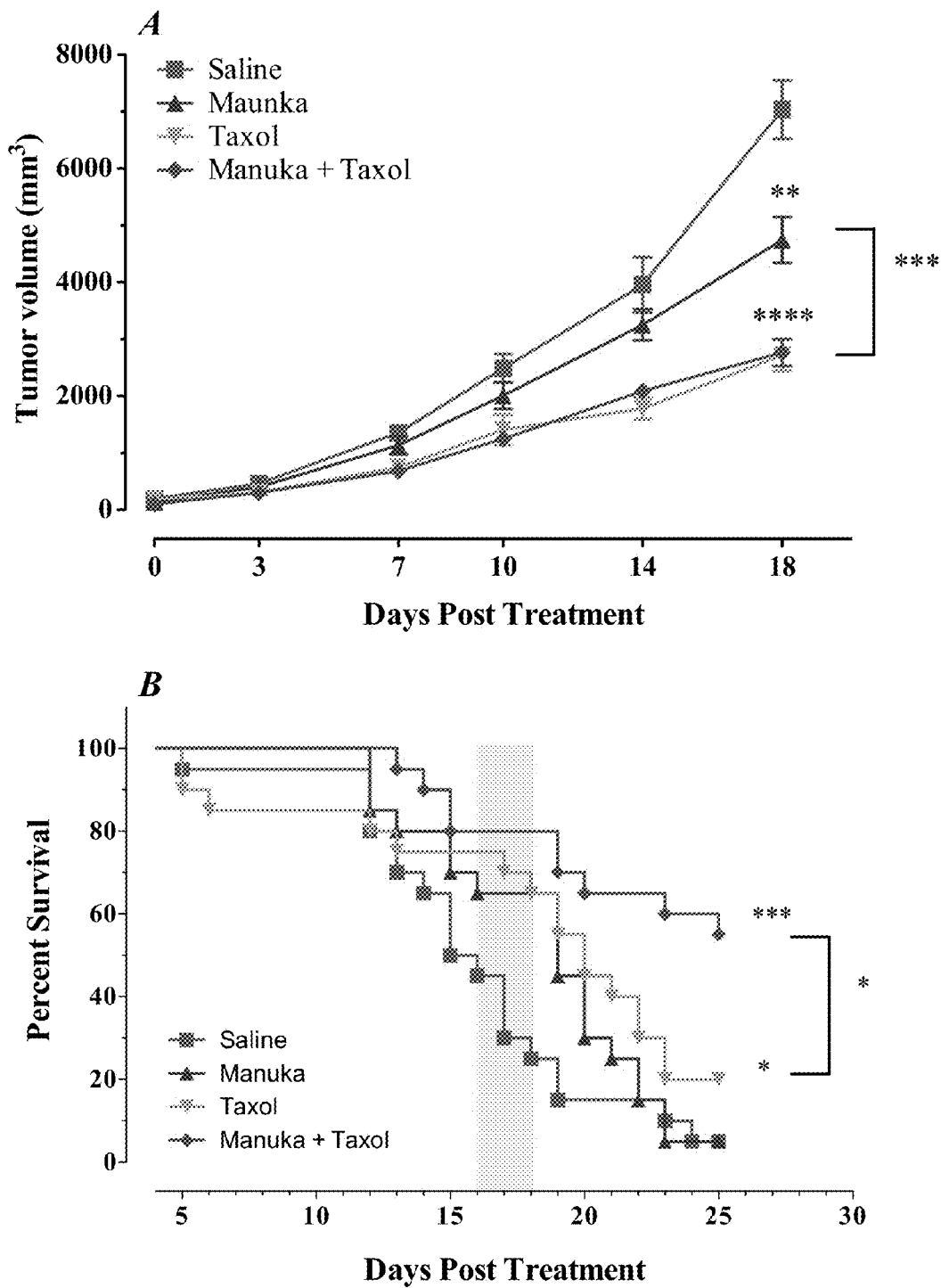
FIG. 8 shows that systemic administration of manuka honey reduces tumor growth and enhances animal survival. (A) Animals with established tumors were treated i.v. with either manuka honey (50% w/v), taxol (10 mg/Kg), manuka honey+taxol, or saline as control. All treatments were given twice per week until the end of observation period. Each data point represents the mean±SEM of 19-20 mice per group, pooled from 2 individual experiments. Asterisks denote statistically significant differences between each experimental group and the saline control group; also shown is a comparison between manuka honey alone and manuka honey+taxol groups (, $p<0.01$; *, $p<0.001$). (B) Co-treatment with taxol and manuka honey leads to a significant enhancement in host survival. Experimental animals were followed for survival for up to day 25 post treatment. Each data point represents the mean±SEM of 19-20 mice per group, pooled from 2 individual experiments. Asterisks denote statistically significant differences between experimental and saline control groups; also shown is a comparison between taxol alone and manuka honey+taxol groups (**, $p<0.01$; *, $p<0.05$).

Systemic Manuka Honey Inhibits Tumor Growth and Enhances Host Survival when Used in Combination with Paclitaxel in a Melanoma Animal Model The antitumor activity of manuka honey was evaluated in the syngeneic B16.F1 melanoma tumor model. C57BL/6 mice with established tumors (mean >50 mm3) were divided into four groups and treated by intravenous administration (2 times per week for up to 3 weeks) of manuka honey alone (50% w/v), taxol alone (10 mg/kg), manuka honey (50% w/v) plus taxol (10 mg/kg) or saline as a control. Tumor volume and animal survival were followed for up to 3 weeks post treatment initiation. As can be seen in FIG. 8A, tumor growth in saline-treated mice occurred continuously and rapidly, reaching a mean of 7035±516 mm3 by day 18 post treatment, which corresponds to day 31 post tumor implantation. Mice treated with manuka honey alone exhibited a significant reduction in tumor volume, with a mean of 4744±403 mm3, representing ~33% inhibition of tumor growth (p=0.0029). Mice treated with taxol alone or manuka honey plus taxol exhibited significantly greater degree of inhibition in tumor growth, with mean tumor volumes being decreased by ~61% compared to control (p=<0.0001). Inhibition of tumor growth in taxol-treated animals was observed as early as 7 days after initiation of treatment, whereas manuka honey-treated mice exhibited a delay in tumor growth starting on day 10 post treatment (FIG. 8A). The effect of the various treatments on animal survival was also followed (FIG. 8B). Median survival for saline control group was ~15 days and great majority of mice (>80%) died by day 19 post treatment. In contrast, manuka honey-treated mice exhibited enhanced survival initially (shaded box in FIG. 8B) with an overall median survival of 19 days. By ~3 weeks, however, their survival declined rapidly, and was ultimately comparable to saline controls at the end of the observation period (day 25 post treatment). Similarly, paclitaxel-treated animals exhibited better survival initially (median survival=20 days) but then declined reaching an overall survival of 20% at the end observation period. Lastly, mice co-treated with manuka honey plus taxol exhibited a marked enhancement in their overall survival with 55% of mice surviving (median>25 days), which was significantly different from controls (p=<0.0001). Taken together, these findings demonstrate that intravenously-administered manuka honey has a modest, but significant, inhibitory effect on the growth of the highly tumorigenic B16.F1 melanoma cells with a transient improvement in host survival. Moreover, when given in conjunction with an optimal dose of taxol, no additive or synergistic effect of manuka honey on overall tumor volume was observed. However, the combination treatment improved overall animal survival dramatically, suggesting perhaps a role for manuka honey in reducing drug-induced toxicity.

Further Studies on the Combination Treatment of Taxol at Different Concentrations and Manuka Honey were Carried Out on B16.F1 Melanoma Tumor Model C57BL/6 mice with established tumors (mean >50 mm$^3$) were divided into four groups and treated by intravenous administration (2 times per week for up to 3 weeks) of manuka honey alone (50% w/v), taxol alone (5 mg/kg), manuka honey (50% w/v) plus taxol (5 mg/kg) or saline as a control. Tumor volume and animal survival were followed for up to 3 weeks post treatment initiation.

Figure 9:
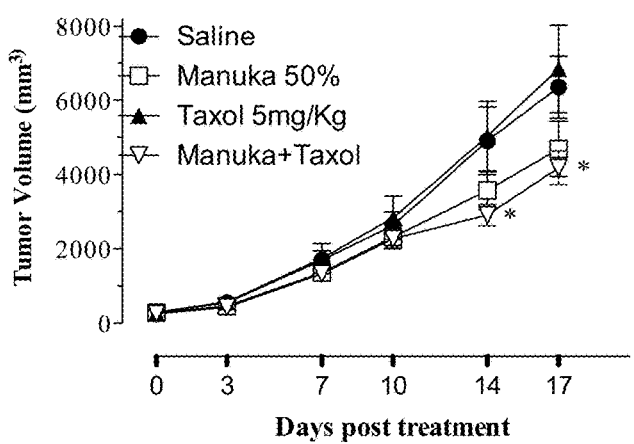
FIG. 9 shows that systemic administration of manuka honey and taxol reduces tumor growth and enhances animal survival. Animals with established tumors were treated i.v. with either manuka honey (50% w/v), taxol (5 mg/Kg), manuka honey+taxol, or saline as control. All treatments were given twice per week until the end of observation period. Asterisk denotes statistically significant differences between the saline control group and manuka honey+taxol group (*, $p<0.05$).

As shown in FIG. 9, administration of taxol at 5 mg/kg was ineffective at reducing tumor volume as compared to the use of saline. However when administered in combination with manuka honey, the combination of taxol and manuka honey was more effective at reducing tumor volume and enhancing survival than the control 14 days post-treatment.

Figure 10:
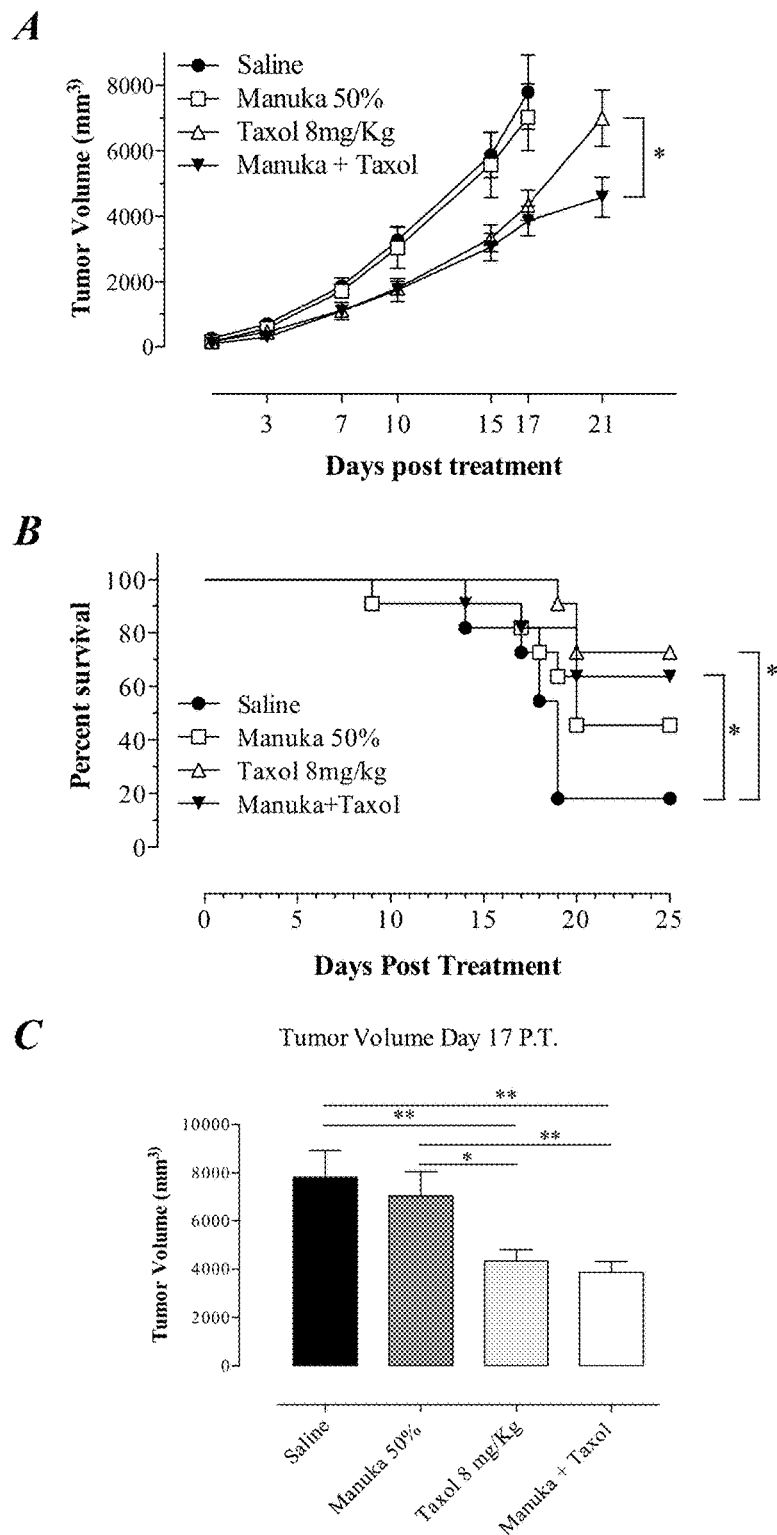
FIGS. 10A-C show that systemic administration of manuka honey and taxol reduces tumor growth (panels A and C) and enhances animal survival (panel B). Animals with established tumors were treated i.v. with either manuka honey (50% w/v), taxol (5 mg/Kg), manuka honey+taxol, or saline as control. All treatments were given twice per week until the end of observation period. (A) Kinetics of tumor growth in the different experimental groups. (B) Host survival was followed for up to day 25 post treatment. (C) Comparison of tumor volumes in the four experimental animals groups at day 17 post treatment. In all panels, asterisks denote significant differences (*, $p<0.05$; **, $p<0.01$).
Figure 11:
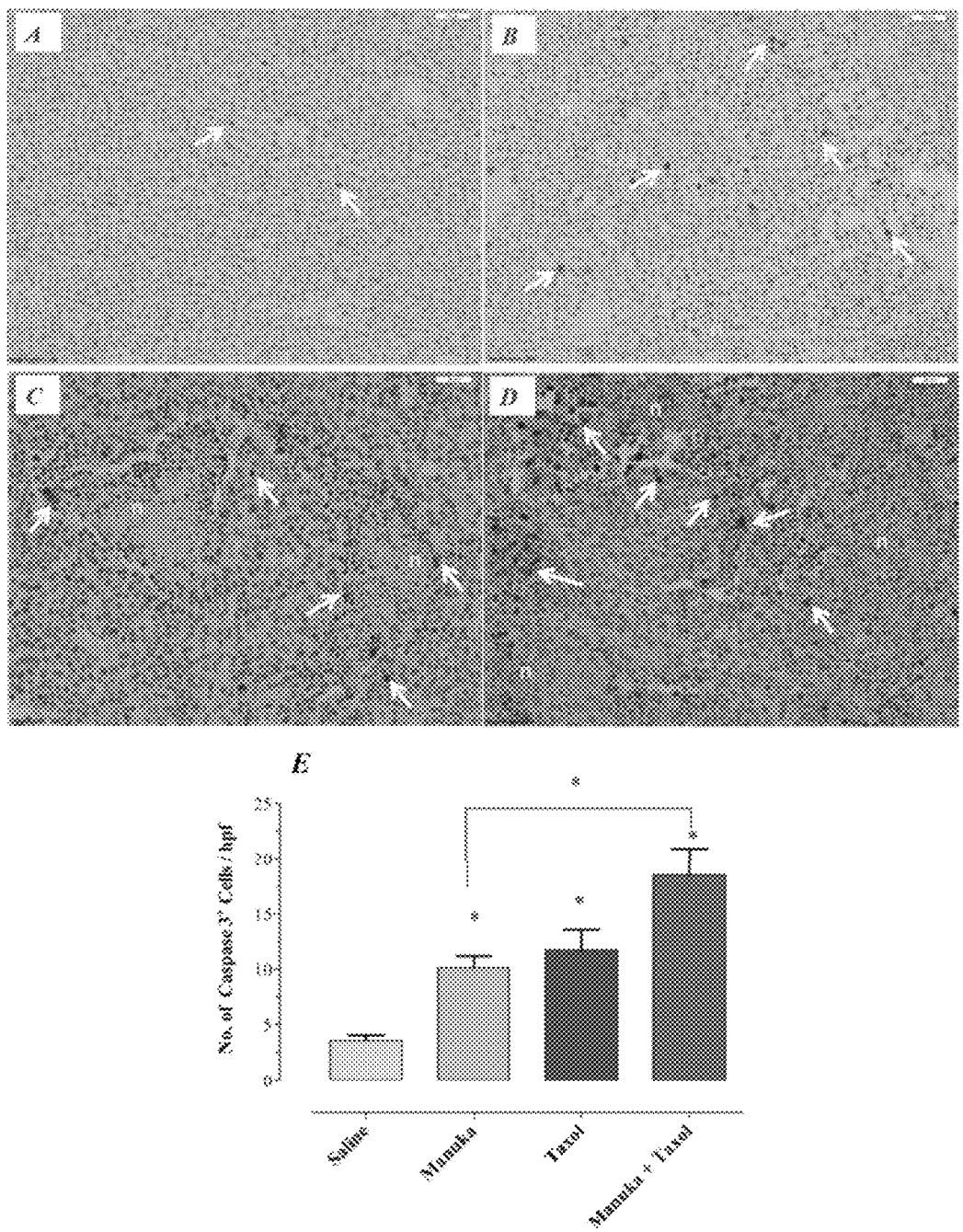
FIG. 11 illustrates the increase in the ratio of caspase 3-positive (apoptotic) tumor cells by direct immunohistochemical staining following treatment with the combination of manuka honey plus paclitaxel. Tumor tissue sections were prepared after treatment with saline (panel A), manuka honey (panel B), paclitaxel (panel C) or manuka honey+paclitaxel (panel D) and stained using caspase 3-specific antibody. Representative images at high magnification (bar=50 μm) are shown. Arrows indicate representative, brown-staining, apoptotic cells. Necrotic regions are also indicated (n). The results are representative of two independent experiments. (E) Quantitative estimation of the number of caspase-3 positive cells in tumor sections of different treatment groups. The data is shown as the mean±SEM of the number of positive cells per high power field. Tumors were obtained from 2-3 mice per treatment group and multiple sections were made from each tumor tissue. The number of positive cells was determined by counting the number of cells in 20 high power fields per section. Asterisks denote statistically significant differences between each experimental group and the saline control group; also shown is a comparison between manuka honey alone and manuka honey+taxol groups (*, $p<0.05$).

In a further experiment the mice were divided into four groups and treated by intravenous administration (2 times per week for up to 3 weeks) of manuka honey alone (50% w/v), taxol alone (8 mg/kg), manuka honey (50% w/v) plus taxol (8 mg/kg) or saline as a control. Tumor volume and animal survival were followed for up to 3 weeks post treatment initiation. As shown in FIGS. 10A-C, the combination of taxol and manuka honey was shown to be effective in inhibiting tumor growth and enhancing survival than the control 14 days post treatment.

Combination In Vivo Treatment with Manuka Honey Plus Paclitaxel Leads to Marked Increase in Cancer Cell Death In Situ Tumor tissue sections were prepared from tumors obtained from animals treated with manuka honey, paclitaxel, manuka honey plus paclitaxel or saline as control. Staining with caspase 3-specific mAb revealed the presence of apoptotic cells, largely concentrated around the perimeter of necrotic tissue (FIG. 11A-D). By counting the number of caspase 3-positive cells in a random selection of 10-20 high power fields (hpf), a quantitative estimate of apoptotic cell number could be achieved. As summarized in FIG. 11E, the number of apoptotic cells in tumors of untreated mice was 3.6±0.4 per hpf. In mice treated with manuka honey or taxol alone, the number of caspase 3-positive cells increased to 10.1±1.0 or 11.7±1.8 per hpf, respectively. In contrast, there was a further increase in the number of apoptotic cells observed in mice treated with taxol plus manuka honey, reaching a mean of 18.5±2.3 per hpf.

Figure 12:
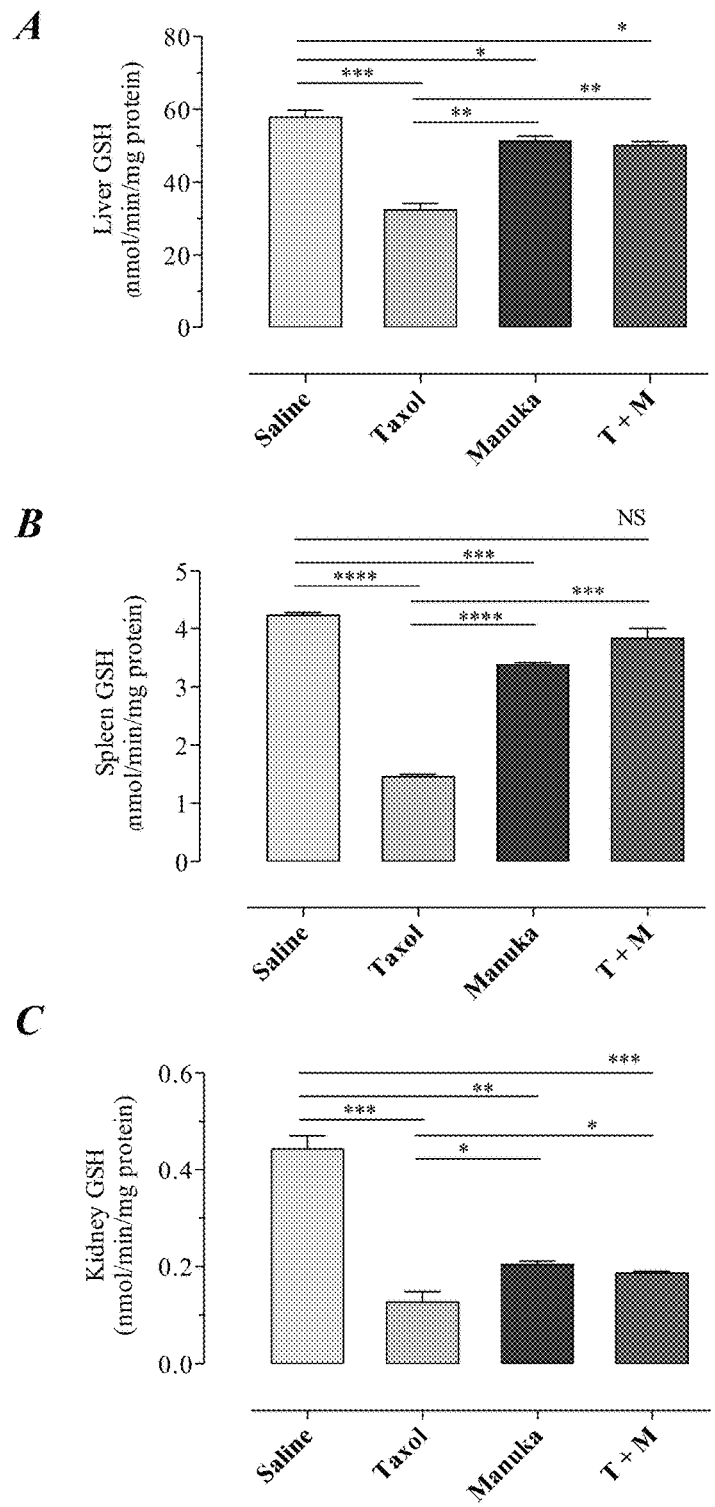
FIGS. 12 A-C demonstrate that manuka honey reverses the systemic, toxic, side-effects of paclitaxel. Animals were treated with saline, paclitaxel, manuka honey or manuka honey plus paclitaxel. At the end of a 3-week treatment, animals were sacrificed and organs removed for toxicity determination. The levels of glutathione (GSH) in the liver (panel A) spleen (panel B) and kidney (panel C) were determined. The data represent the mean±SEM of a minimum of 3 determinations per experimental group. For all panels, asterisks denote significant differences between the indicated groups (*, $p<0.05$; , $p<0.01$; *, $p<0.001$).

Systemic Administration of Manuka Honey Reverses Paclitaxel-Induced Organ Toxicity Groups of mice were injected with manuka honey, paclitaxel, manuka honey plus paclitaxel or saline for a total period of 3 weeks (2 injections per week). The animals were then sacrificed and their organs (liver, spleen, and kidney) obtained and analyzed for the levels of glutathione (GSH), a major antioxidant effector. The levels of GSH in each organ are shown in FIGS. 12A-C. The findings illustrate that paclitaxel treatment results in a marked decrease in organ GSH levels, specifically in the liver and spleen. In sharp contrast, treatment with a combination of manuka honey plus paclitaxel largely reversed the decrease in organ GSH levels. These results demonstrate unequivocally the ability of manuka honey to protect against the systemic toxicity induced by paclitaxel.

In the present study, a melanoma murine model known for its low immunogenicity, and hence high tumorigenicity, was used to demonstrate a role for manuka honey in retarding tumor growth in vivo. Histological and immunohistochemical evidence is provided to show that tumor retardation correlated with increased apoptosis of tumor cells. More intriguingly, the findings demonstrate that simultaneous treatment with a chemotherapeutic drug plus manuka honey led to a highly significant improvement in overall animal survival. This suggests that the advantage of using intravenous manuka honey may well extend beyond its direct antitumor activity to include the added beneficial effect of reducing chemotherapy drug-induced toxicity and enhancing host survival.

The main mechanism by which manuka honey appears to exert its anti-proliferative effect on cancer cells is through the activation of the intrinsic apoptotic pathway, involving the induction of the initiator caspase-9 which in turns activates the executioner caspase-3. In contrast, no evidence for the activation of caspase-8, and hence the extrinsic pathway, in manuka-treated cancer cells. In contrast, essentially the reverse was observed in taxol-treated cells where caspase-8, but not caspase-9, activation was evident. This is in line with previous reports showing that taxol's effect on cell growth was mediated mainly through the extrinsic apoptosis pathway without the involvement of caspase-9. Manuka honey-induced apoptosis is also associated with the activation of PARP, induction of DNA fragmentation and loss of Bcl-2 expression. The results of the in vitro cell viability studies demonstrate that manuka honey was effective against several types of murine and human cancer cell lines at very low concentrations. The IC50 values (manuka concentrations required for 50% inhibition of cell growth) of the murine B16.F1 melanoma cells, calculated after 24, 48 or 72 hrs of exposure to manuka honey were 2%, 1.3% and 0.8%, respectively. Similarly, for CT26 cells, the IC50 values at 24 and 72 hrs were 2% and 1%. Interestingly, the observed IC50 values for MCF-7 cells are significantly higher, calculated to be >5% and 4% manuka honey at 24 and 72 hr, respectively. The observed relative resistance of the MCF-7 cells to manuka honey-induced apoptosis may well be due to the fact that these cells are known to be deficient in caspase-3 expression (Janicke R U (2009) *Breast Cancer Res Treat* 117: 219-221, Janicke R U et al (1998) *J Biol Chem* 273: 9357-9360). Nevertheless, it is intriguing to hypothesize that the fact that manuka honey could still induce apoptosis in caspase-3-deficient cells may well indicate that a secondary pathway could also function, albeit at reduced efficiency.

The ability of manuka honey, at concentrations as little as 0.3-0.6%, were found to induce apoptosis in cancer cells. This was demonstrated using several approaches, including cell viability and flowcytometric assays, direct determination of increased caspase 3/7 and 9 enzyme activities, and DNA fragmentation. Moreover, using a syngeneic melanoma model, it was demonstrated that manuka honey was also effective against cancer cells in vivo, as evidenced by the observed decrease in tumor volume and increased apoptosis of tumor cells detected by caspase-3 immunohistochemical analysis. Although detailed analyses of the effect of other types of honey on cancer cells remain to be done, based on the cell viability data, the results suggest that manuka honey may be superior in its anticancer potential than other types of honey. Using Tualang honey, Ghashm and coworkers reported IC50 values of 3.5-4.0% against human oral squamous cell carcinoma and osteosarcoma cell lines. Swellam et al also reported IC50 values of 2.0-4.0% against bladder cancer cell lines using unfractionated honey from Manitoba, Japan These differences are most likely due to variations in honey content, particularly in polyphenols and phenolic acids with known antitumor activities. Scientific evidence for the use of honey in wound healing has been accumulating over the past few years, largely as a result of completed small-scale clinical trials. Many properties of honey have been described that aid the process of wound healing such as activating the innate immune system, inducing the migration of neutrophils and macrophages, promoting the debridement of devitalized tissue, stimulating angiogenesis and granulation, and preventing infection. Manuka honey has the capacity to stimulate macrophages to release innate immune mediators, such as TNF-$\alpha$, IL-1$\beta$ and IL-6, which are essential for tissue healing and for limiting microbial infections.

The present invention has found that there is a beneficial effect of administering manuka honey together with taxol. In comparison with the animal group receiving taxol alone, those treated with taxol and manuka honey exhibited a highly significant improvement in survival. This occurred despite having almost identical mean tumor volumes in both experimental groups, suggesting there was no added or synergistic action of both agents on inhibiting tumor growth, at least at the optimal dose of taxol used in this study. These findings suggest that manuka honey administration may decrease the toxic side effects of chemotherapeutic drugs. Support for this hypothesis is evident in recently published reports demonstrating potent antiinflammatory, antioxidant and cell growth-promoting activities among various types of honey, including manuka honey. Moreover, intravenous administration of honey protected against organ failure in rabbits following LPS-induced sepsis through the inhibition of inflammation and myeloperoxidase production. Thus, manuka honey may well improve survival of taxol treated, tumor-bearing, mice via a similar protective mechanism. The current findings should facilitate further work to examine whether manuka honey could synergize with, or be a substitute for, chemotherapeutic drugs given at sub-optimal doses for cancer therapy.

What is claimed:

1. An intravenous pharmaceutical composition comprising:
   a diluent;
   at least 50% w/v of manuka honey diluted by the diluent; and
   at least one chemotherapeutic agent, wherein the chemotherapeutic agent is one of paclitaxel and any pharmaceutically acceptable salts thereof, and wherein the chemotherapeutic agent is provided in an amount of at least about 10 mg/kg of a patient to be treated.

2. The pharmaceutical composition of claim 1, wherein the pharmaceutical composition is in the form of a solution.

3. A method of treating skin, colon, and/or breast cancer in a patient comprising administering to the patient a pharmaceutically acceptable amount of a pharmaceutical composition comprising the composition of claim 1.

4. The method of claim 3, further comprising administering a second chemotherapeutic agent.

5. The method of claim 4, wherein the second chemotherapeutic agent is at least one of cisplatin, doxorubicin, trastuzumab, and any pharmaceutically acceptable salts thereof.

6. The method of claim 3, wherein the pharmaceutical composition is administered intravenously.

7. The pharmaceutical composition of claim 1, wherein the diluent is a sterile saline solution.

8. A unit dose or multi-dose container containing the intravenous pharmaceutical composition as claimed in claim 1.

9. The pharmaceutical composition of claim 1, wherein the composition is for enhancing survival of the patient.

* * * * *